United States Patent [19]  
Herbst et al.

[11] 3,943,148  
[45] Mar. 9, 1976

[54] INDOLE FUSED HETEROCYCLIC DIURETIC COMPOUNDS

[75] Inventors: David R. Herbst, Wayne; Herchel Smith, Bryn Mawr, both of Pa.

[73] Assignee: American Home Products Corporation, New York, N.Y.

[22] Filed: Aug. 10, 1972

[21] Appl. No.: 279,411

Related U.S. Application Data

[60] Division of Ser. No. 38,913, May 19, 1970, abandoned, which is a continuation-in-part of Ser. No. 889,867, Dec. 22, 1969, abandoned, which is a continuation-in-part of Ser. No. 839,629, July 7, 1969, abandoned, which is a continuation-in-part of Ser. No. 632,105, April 19, 1967, abandoned, which is a continuation-in-part of Ser. No. 536,076, Feb. 21, 1966, abandoned, which is a continuation-in-part of Ser. No. 428,842, Jan. 28, 1965, abandoned.

[52] U.S. Cl.......... 260/326.5 B; 260/326.9; 424/274  
[51] Int. Cl.²............... C07D 209/12; C07D 209/14  
[58] Field of Search . 260/326.9, 326.5 B, 326.5 CA

[56] References Cited  
UNITED STATES PATENTS  
3,478,051  11/1969  Houlihan et al. ................ 260/326.9

OTHER PUBLICATIONS  
Wenkurt et al., Can. J. Chem. Vol. 42, pp. 489–490 (1964).  
Herbst et al., J. Med. Chem. Vol. 9, pp. 864–868 (1966).

Primary Examiner—Paul M. Coughlan, Jr.  
Attorney, Agent, or Firm—David E. Frankhouser

[57] ABSTRACT

Substituted 1,2,4,5,6,7,8,9-octahydro-3H-azecino[5,4-b]-indoles and substituted 1,2,3,4,5,6,7,8-octahydroazonino[5,4-b]-indoles are prepared by cleavage of the corresponding quaternary alkyl iodide salts with lithium in liquid ammonia. The products possess diuretic activity.

6 Claims, No Drawings

INDOLE FUSED HETEROCYCLIC DIURETIC COMPOUNDS

This application is a divisional of copending U.S. patent application, Ser. No. 38,913, filed May 19, 1970, now abandoned; which is a continuation-in-part of U.S. patent application Ser. No. 889,867, filed Dec. 22, 1969, now abandoned; which is a continuation-in-part of copending U.S. patent application Ser. No. 839,629, filed July 7, 1969, now abandoned; which is a continuation-in-part of U.S. patent application Ser. No. 632,105, filed Apr. 19, 1967, now abandoned; which is a continuation-in-part of U.S. patent application Ser. No. 536,076, filed Feb. 21, 1966, now abandoned; which is a continuation-in-part of U.S. patent application Ser. No. 428,842, filed Jan. 28, 1965, now abandoned.

This invention relates to indole derivatives having valuable pharmacological activity. More particularly, this invention relates to substituted 1,2,4,5,6,7,8,9-octahydro-3$\underline{H}$-azecino[5,4-b]indoles and to substituted 1,2,3,4,5,6,7,8-octahydroazonino[5,4-b]indoles which in standard pharmacological tests demonstrate activity as diuretic agents.

The invention sought to be patented comprises chemical compounds of the formula:

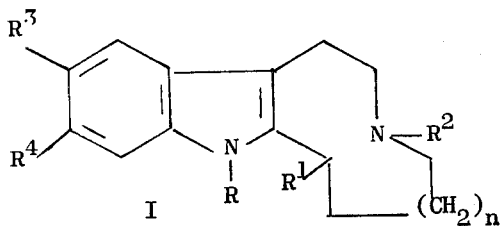

wherein R is hydrogen or lower alkyl; $R^1$ is hydrogen, lower alkyl, or phenyl; $R^2$ is lower alkyl; $R^3$ and $R^4$ are, independently, hydrogen or lower alkoxy; and $n$ is 1 or 2; and the non-toxic pharmaceutically acceptable acid addition salts thereof; with the proviso that at least one of $R^3$ and $R^4$ must be hydrogen.

In a subgeneric aspect, the invention comprises the compounds of Formula I where R is hydrogen, $R^1$ is lower alkyl or phenyl, and $R^2$, $R^3$, $R^4$, and n have the meanings set forth in Formula I, and the non-toxic pharmaceutically acceptable acid addition salts thereof.

In a second subgeneric aspect, the invention comprises the compounds of Formula I where R is lower alkyl, $R^1$ is hydrogen, lower alkyl, or phenyl, and $R^2$, $R^3$, $R^4$ and n have the meanings set forth in Formula I, and the non-toxic pharmaceutically acceptable acid addition salts thereof.

In a third subgeneric aspect, the invention comprises compounds of Formula I where R and $R^1$ are hydrogen, and $R^2$, $R^3$, $R^4$ and n have the meanings set forth in Formula I, and the non-toxic pharmaceutically acceptable acid addition salts thereof.

Typical examples of the compounds of Formula I are the following:

i. 1,2,4,5,6,7,8,9-octahydro-3-methyl-3$\underline{H}$-azecino-[5,4-b]indole;
ii. 1,2,4,5,6,7,8,9-octahydro-3,9-dimethyl-3$\underline{H}$-azecino[5,4-b]indole;
iii. 1,2,3,4,5,6,7,8-octahydro-3-methylazonino-[5,4-b]indole;
iv. 1,2,3,4,5,6,7,8-octahydro-3,8-dimethylazonino-[5,4-b]indole;
v. 1,2,3,4,5,6,7,8-octahydro-3,7-dimethylazonino-[5,4-b]indole;
vi. 1,2,3,4,5,6,7,8-octahydro-3-methyl-7-phenyl-azonino[5,4-b]indole;
vii. 1,2,3,4,5,6,7,8-octahydro-3,7,8-trimethylazonino[5,4-b]indole; and
viii. 1,2,3,4,5,6,7,8-octahydro-11-methoxy-3,7,8-trimethylazonino[5,4-b]indole;

and the non-toxic pharmaceutically acceptable acid addition salts thereof.

The aforesaid compounds in the form of the non-toxic, acid-addition salts thereof with pharmacologically acceptable acids, may be prepared by dissolving the specific compound in the free base form, which has been prepared by the methods described generally above, in a suitable organic solvent, and treating it with an alcoholic solution of the selected acceptable acid, in accordance with conventional procedures for preparing acid-addition salts from base compounds generally. As such acids, there may be used any of hydrochloric, hydrobromic, tartaric, phosphoric, maleic, citric, acetic, benzoic, or other pharmacologically acceptable acid.

In the pharmacological evaluation of the compounds of Formula I, the in vivo diuretic effects are tested by the procedure described by Lipschitz et al., *J. Pharmacol.*, 79:97 (1943), which is as follows:

Male Sprague-Dawley rats 14 to 17 weeks old, 175–200 gms. are deprived of food and water from 4 p.m. on the day before an experiment. The next morning, the rats are given an oral physiological saline prime dose of 25 ml./kg. The test compound is administered orally or peritoneally. Each compound is given to eight rats. Urea at a dose of 960 mg./kg. is given as a standard of comparison to eight rats, and saline alone is given to eight more rats as a control. The animals are placed in metabolism cages, two rats per cage, and urine is collected for five hours. Volume, sodium and potassium are determined. Results are expressed as a ratio of Test/Urea (T/U). A compound having a ratio greater than 1.00 for volume and 1.00 for sodium is considered active.

When the compounds of this invention are tested as described above, they exhibit diuretic activity when administered at a dose of 25 mg/kilo of body weight.

When the compounds of this invention are employed pharmaceutically, i.e. as diuretic agents, they may be administered alone or in combination with pharmacologically acceptable carriers, the proportion of which is determined by the solubility and chemical nature of the compound, chosen route of administration and standard pharmacological practice. For example, they may be administered orally in the form of tablets or capsules containing such excipients as magnesium stearate, lactose, sugar, and so forth. They may be administered orally in the form of solution or they may be injected parenterally, e.g. intramuscularly. For parenteral administration, they may be used in the form of a sterile solution or suspensions containing other solutes, for example, enough saline or glucose to make the solution isotonic.

The dosage of the present pharmacologically active agents will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

The compounds of Formula I are prepared by cleavage of a compound of the formula:

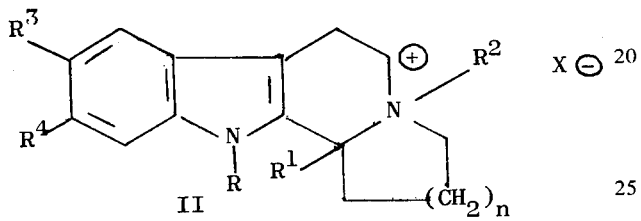

where R, $R^1$, $R^2$, $R^3$, $R^4$ and $n$ have the meanings set forth in Formula I, and X is a halide, e.g. the chloride, bromide, or iodide anion. The cleavage reaction is effected by contacting the quaternary alkyl halide compound (II) with an alkali metal, such as lithium, in liquid ammonia and a lower alkanol, preferably 1-methoxy-2-propanol.

The quaternary alkyl halide compounds of Formula II are prepared in a known manner by the quaternization of a compound of the formula:

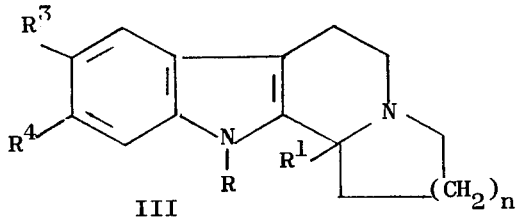

where R, $R^1$, $R^3$, $R^4$ and n have meanings set forth in Formula I. The quaternization is effected by treating the base (III) with a quaternizing agent, preferably a lower alkyl halide, following the procedure described by W. Reckhlow, et al., J. Am. Chem. Soc., 74, 4962 (1952).

The compounds of Formula III are known compounds or can be prepared by known methods or obvious modifications thereof.

The compounds of Formula III where R and $R^1$ are hydrogen, i.e. 2,3,5,6,11,11b-hexahydro-1H-indolizino[8,7-b]indole and 1,2,3,4,6,7,12,12b-octahydroindolo[2,3-a]quinolizine or the phenyl-substituted lower alkoxy derivatives thereof, can be prepared according to the methods described by K. Nagarajan et al., Helv. Chim. Acta., 46, 1221 (1963). Said compounds can be alkylated to afford the corresponding $N_{ind}$-(lower)alkyl compounds (i.e. the compounds of Formula III where R is lower alkyl and $R^1$ is hydrogen) by reaction with an alkylating agent (e.g. a lower alkyl halide or tosylate) in the presence of a base (e.g. sodium hydride) in a reaction inert solvent at a temperature ranging from about 0°C to about 100°C for a period of time ranging up to 6 hours.

The compounds of Formula III where R is hydrogen and $R^1$ is lower alkyl or phenyl are prepared according to the methods described by S. Wawzonek et al. J. Med. Chem., 8, 265 (1965); F. Shiroyan et al., Arm. Khim. Zh., 20, 649 (1967); or F. Shiroyan, et al. Arm. Khim. Zh., 21, 1025 (1968). Said compound can be alkylated to afford the corresponding $N_{ind}$-(lower)alkyl compounds (i.e. the compounds of Formula III where R is lower alkyl and $R^1$ is lower alkyl or phenyl) by employing the alkylation procedure heretofore described.

Alternatively the compounds of Formula III where R is lower alkyl and $R^1$ is lower alkyl or phenyl can be prepared from a lactam of the formula:

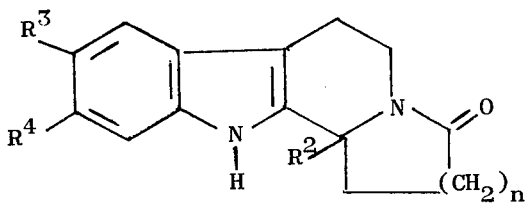

produced according to the methods described by S. Wawzonek, or F. Shiroyan, supra, by $N_{ind}$-alkylation of the lactam followed by reduction of the lactam keto group with a reducing agent, e.g. lithium aluminum hydride in tetrahydrofuran.

As employed herein, the terms "lower alkyl" and "lower alkoxy" are meant to include straight chain hydrocarbon substituents having from one for four carbon atoms, i.e. the methyl, ethyl, propyl, or butyl groups.

The best modes contemplated by the inventor for the manner and process of making the compounds of this invention are hereinafter described:

EXAMPLE I 1,2,4,5,6,7,8,9-Octahydro-3-methyl-3H-azecino-[5,4-b]indole, hydrochloride a. To 1.8 l. liquid ammonia (distilled from sodium) are added 9.48 g. crude 1,2,3,4,6,7,12,12b-octahydro-5-methylindolo[2,3-a]quinolizinium iodide [W. A. Reckhow and D. S. Tarbell, J. Am. Chem. Soc., 74, 4962 (1952)], followed by addition of 2.55 g. 1-methoxy-2-propanol (2.76 ml.) and 0.39 g. lithium. After six minutes, the blue color is gone, 2.0 ml. water are added with caution and the ammonia is evaporated by warming under a nitrogen stream. The residue is thoroughly extracted with chloroform and the extracts are washed with brine and freed of solvent. Chromatographic purification of the resultant gum on activity III neutral alumina affords 3.31 g. of the crude product, decomposition 92.0°–94.5°C. Two recrystallizations of a 200 mg. portion of this material from hexane gives 1,2,4,5,6,7,8,9-octahydro-3-methyl-3H-azecino[5,4-]indole, decomposition 95°–97°C. The nuclear magnetic resonance spectrum of the final product indicates the presence of three N-methyl protons but no C-methyl protons.

Analysis: $C_{16}H_{22}N_2$: Calculated: C, 79.29; H, 9.15; N, 11.56. Found: C, 79.44; H, 9.27; N, 11.46.

b. Three grams of the crude product obtained in (a) and having decomposition at 92.0°–94.5°C., are dissolved in ether and treated with excess isopropanolic hydrogen chloride. Two crystallizations of the salt from a mixture of methanol and ethyl acetate yield 1,2,4,5,6,7,8,9-octahydro-3-methyl-3H-azecino-[5,4-b]indole, hydrochloride, hemi-hydrate, softens 135°C. decomposition 145°–150°C.

Analysis: $C_{16}H_{22}N_2 \cdot HCl \cdot \frac{1}{2} H_2O$: Calculated: C, 66.76; H, 8.40; Cl, 12.32; N, 9.74. Found: C, 66.55; H, 8.42; Cl, 12.5; N, 9.81.

EXAMPLE II

1,2,4,5,6,7,8,9-Octahydro-3,9-dimethyl-3H-azecino[5,4-b]indole a. A solution of 4.97 g. 1,2,3,4,6,7,12,12b -octahydro-12-methylindolo[2,3-a]quinolizine (prepared by the method of Example IV-(a) [T. Oshi et al., *Chem. Pharm. Bull.* (Tokyo), 11, 1196 (1963)] in 200 ml. ethyl acetate is stirred with 22.79 g. methyl iodide for 1 hour. After dilution with 200 ml. ether and stirring at about 0°C. for 1 hour, the reaction mixture is filtered. The solids are thoroughly washed with ether and dried to give 6.59 g. salt, decomposition 259°–262°. A 400 mg. portion of this product is twice recrystallized from methanol to provide 210 mg. 1,2,3,4,6,7,12,12b-octahydro-5,12-dimethylindolo[2,3-a]-quinolizinium iodide, decomposition 264°–267°; $\lambda_{max}^{95\% EtOH}$ 222.5 ($\epsilon$ 53,400), 280–285 plateau ($\epsilon$ 7,400), and 290–293 plateau ($\epsilon$ 6,300) mm; $\lambda_{min}^{95\% EtOH}$ 248 (2,000) mm.

Analysis: $C_{17}H_{23}N_2I$: Calculated: C, 53.4; H, 6.1; I, 33.2; N, 7.3. Found: C, 53.1; H, 6.4; I, 33.4; N, 6.95.

b. Treatment of 1,2,3,4,6,7,12,12b-octahydro-5,12-dimethylindolo[2,3-a]quinolizinium iodide, obtained as in (a) above, with lithium, ammonia, and 1-methoxy-2-propanol in the manner described in Example III(b), gives 1,2,4,5,6,7,8,9-octahydro-3,9-dimethyl-3H-azecino[5,4-b]indole as an oil, further characterized as the hydrochloride salt, m.p. 221°–223°C. (decomposition).

Analysis: $C_{17}H_{24}N_2 \cdot HCl$: Calculated: C, 69.7; H, 8.6; Cl, 12.1; N, 9.6. Found: C, 69.5; H, 8.9; Cl, 12.1; N, 9.15.

EXAMPLE III

1,2,3,4,5,6,7,8-Octahydro-3-methylazonino[5,4-b]indole a. A solution of 1.12 g. of 2,3,5,6,11,11b-hexahydro-1H-indolizono[8,7-b]indole [K. Nagarajan, Ch. Weissman, H. Schmid and P. Karrer, *Helv. Chem. Acta.*, 46, 1221 (1963)], in 65 ml. ethyl acetate is treated with 3.19 g. methyl iodide. After standing 2 hours at 25°C., the product is collected, washed with ether and crystallized from a methanol and ether system and from methanol (twice) to give 2,3,5,6,11,11b-hexahydro-4-methyl-1H-indolizino[8,7-b]indole, iodide, decomposition 183.5°–187.5°C. Two additional crystallizations from methanol afford an analytically pure product, decomposition 184.5°–187.5°C.

Analysis: $C_{15}H_{19}IN_2$: Calculated: C, 50.86; H, 5.41; I, 35.83; N, 7.91. Found: C, 50.55; H, 5.67; I, 35.5; N, 7.63.

b. To a mixture of 100 ml. ammonia (distilled from lithium), 0.35 g. 2,3,5,6,11,11b-hexahydro-4-methyl-1H-indolizino[8,7-b]indolium, iodide, prepared as in (a) above, and 0.11 g. 1-methoxy-2-propanol are added 15 mg. lithium. The vigorously stirred mixture immediately becomes deep blue, but after 5 minutes the color fades. After stirring 5 minutes longer, 1 ml. water is added, the milky suspension is freed of ammonia under a nitrogen stream (with cautious warming), and the residue is thoroughly extracted with ether. The ethereal solution is washed with brine and solvent is removed to give 0.18 g. crude product, m.p. 128°–131°C. Two crystallizations from n-hexane produce 0.13 g. 1,2,3,4,5,6,7,8-octahydro-3-methylazonino[5,4-b]indole, m.p. 130°–132°C. The nuclear magnetic resonance spectrum of the product shows the presence of N-methyl protons but no C-methyl protons.

Analysis: $C_{15}H_{20}N_2$: Calculated: C, 78.90; H, 8.83; N, 12.27. Found: C, 79.06; H, 8.93; N, 12.25.

EXAMPLE IV

1,2,3,4,5,6,7,8-Octahydro-3,8-dimethylazonino[5,4-b]indole a. 2,3,5,6,11,11b-Hexahydro-1H-indolizino[8,7-b]-indole (8.49 g.) is stirred for 1 hour at 25°C. in dimethylformamide (200 ml.) containing sodium hydride (2.11 g. of a 50% mineral oil dispersion). Methyl iodide (6.25 g.) in dimethylformamide (25 ml.) is added and the mixture is stirred at 25°C. for 16 hours. The dimethylformamide is distilled off, and the residue is dissolved in chloroform and washed with aqueous potassium bicarbonate and water, and dried. The product is chromatographed on neutral alumina to give 2,3,5,6,11,11b-hexahydro-11-methyl-1H-indolizino[8,7-b]indole as a clear oil (5.88 g.).

The base is converted by dissolution in ether and treatment with isopropanol saturated with hydrogen chloride into the hydrochloride salt, m.p. 244°–247.5°C. (from acetone).

Analysis: $C_{15}H_{18}N_2 \cdot HCl$: Calculated: C, 68.55; H, 7.3; Cl, 13.5; N, 10.7. Found: C, 68.6; H, 7.1; Cl, 13.7; N, 10.9.

b. 2,3,5,6,11,11b-hexahydro-11-methyl-1H-indolizino-[8,7-b]indole (5.96 g.), obtained as in (a) above, is stirred for one hour at 25° in ethyl acetate (125 ml.) containing methyl iodide (22.8 g.). The mixture is diluted with ether (100 ml.) and kept at 0°C. for one hour to give 2,3,5,6,11,11b-hexahydro-4,11-dimethyl-1H-indolizino[8,7-b]indolium, iodide as a buff solid (7.08 g.), m.p. 249°–252°C. (decomposition). An aliquot after two recrystallizations from methanol has m.p. 254°–256°C.

Analysis: $C_{16}H_{21}N_2I$: Calculated: C, 52.2; H, 5.75; N, 7.6; I, 34.5. Found: C, 52.45; H, 5.8; N, 7.6; I, 34.3.

c. Treatment of 2,3,5,6,11,11b-hexahydro-4,11-dimethyl-1H-indolizino[8,7-b]indolium, iodide with lithium, ammonia, and 1-methoxy-2-propanol in the manner of Example III(b) gives 1,2,3,4,5,6,7,8-octahydro-3,8-dimethylazonino[5,4-b]indole, as a clear oil, further characterized as the hydrochloride salt, m.p.

198.5°–201°C. (from acetone).

Analysis: $C_{16}H_{22}N_2 \cdot HCl$: Calculated: C, 68.9; H, 8.3; Cl, 12.7; N, 10.05. Found: C, 68.8; H, 8.1; Cl, 13.0; N, 9.8.

EXAMPLE V 1,2,3,4,5,6,7,8-Octahydro-3,7-dimethylazonino[5,4-b]-indole, hydrochloride, hemihydrate a. A solution of 9.28 g. of 2,3,5,6,11,11b-hexahydro-11b-methyl-1H-indolizino[8,7-b]indole [S. Wawzonek and J. D. Nordstrom, *J. Med. Chem.*, 8, 265 (1965)] in 100 ml. benzene is refluxed with 25.6 ml. methyl iodide for one-quarter hour. After cooling to 10°C., the solids are collected, washed with ether and dried. Crystallization (twice) of 3.5 g. of the salt from methanol affords 2.95 g. of white, crystalline, 2,3,5,6,11,11b-hexahydro-4,11b-dimethyl-1H-indolizino[8,7-b]-indolium iodide, decomposition 250°–254°C.

b. Treatment of 10.11 g. 2,3,5,6,11,11b-hexahydro-4,11b-dimethyl-1H-indolizino[8,7-b]indolium iodide with 774 mg. lithium, 3.97 g. 1-methoxy-2-propanol and 2 liters liquid ammonia in the manner described in Example I-(a) gives 4.04 g. base as an amber oil. Distillation of a 200 mg. portion at 120°–130°C./0.2 mm yields 185 mg. 1,2,3,4,5,6,7,8-octahydro-3,7-dimethylazonino[5,4-b]indole, NMR ($CDCl_3$): δ 1.28 (doublet, J 7 cps., 7-methyl), 2.43 (singlet, 3-methyl) ppm. The remainder of the amber oil, in anhydrous ether, is converted to a salt with isopropanolic HCl. Two crystallizations of the salt from acetone produce 1.99 g. of the title compound, decomposition at 240°–245°C. (shrinks 154°C.).

EXAMPLE VI 1,2,3,4,5,6,7,8-Octahydro-3-methyl-7-phenylazonino[5,4-b]indole

Following the method of Example V, 8.66 g. 2,3,5,6,11,11b-hexahydro-11b-phenyl-1H-indolizino[8,7-b]indole [S. Wawzonek and J. D. Nordstrom, *J. Med. Chem.*, 8, 265 (1965)] are converted to 9.9 g. of salt. Two crystallizations of a 3.5 g. quantity of salt from methanol afford 2.16 g. of 2,3,5,6,11,11b-hexahydro-4-methyl-11b-phenyl-1H-indolizino[8,7-b]indolium iodide as white needles, decomposition 271°–273°C.

Then 2,3,5,6,11,11b-hexahydro-4-methyl-11b-phenyl-1H-indolizino[8,7-b]indolium iodide (8.09 g.), 286 mg. lithium, 2.03 g. 1-methoxy-2-propanol and 2 liters liquid ammonia are reacted according to the method of Example I-(a). The white foam isolated from the 1:9 and 1:4 benzene-hexane elutes is crystallized from hexane to provide 4.38 g. base. A 300 mg. portion is crystallized (twice) from hexane thereby yielding 200 mg. of title compound, m.p. 117°–119°C., NMR ($CDCl_3$): δ 2.45 (singlet, 3-methyl), 5.70 (triplet, J 8 cps., 7-hydrogen) ppm.

EXAMPLE VII 1,2,5,6,11,11b-Hexahydro-11b-methyl-3H-indolizino[8,7-b]indol-3-one Tryptamine (112.15 g.), levulinic acid (97.6 g., 85.6 ml.) and butyl cellosolve (1 liter) are refluxed under nitrogen for 16 hours and the solvent is removed. The residue is successively washed with water, dilute aqueous sodium hydroxide, water, dilute aqueous hydrochloric acid, water and dried. Trituration of the crude product, decomposition at 252°–262°C., with methanol, and then with benzene, and drying provides 120.4 g. of the title compound, decomposition at 259°–263°C.; $\lambda_{max}^{KBr}$ 3.09, 6.01, 6.17, 13.38 μ.

EXAMPLE VIII 1,2,5,6,11,11b-Hexahydro-11,11b-dimethyl-3H-indolizino[8,7-b]indol-3-one A suspension of 4.81 g. 1,2,5,6,11,11b-hexahydro-11b-methyl-3H-indolizino[8,7-b]indol-3-one in 100 ml. dry dimethylformamide (DMF) is stirred under nitrogen with 1.06 g. of about 50% sodium hydride-mineral oil dispersion for 0.5 hour as hydrogen is evolved. The reaction solution is cooled in an ice-water bath as 3.41 g. methyl iodide (1.50 ml.) are added dropwise. After stirring for 0.5 hour at 0°, the cooling bath is removed and the mixture is kept at about 25° for 18 hours. After removal of solvent (in vacuo), the crude product is dissolved in chloroform, washed with water and dried with sodium sulfate. The solvent is removed and the residue is chromatographically purified on a 250 g. column of neutral, activity III alumina. The product isolated from the 1:4 and 1:1 ether-benzene eluates is crystallized from carbon tetrachloride (twice) and from ethyl acetate to afford 2.63 g. of the title compound, m.p. 131.5°–4.5°C.; $\lambda_{max}^{KBr}$ 5.94 μ; $\lambda_{max}^{95\% EtOH}$ 226.5 (ε 34,100), 276 sh (ε 5,980), 282 (ε 6,360), 290 sh (ε 5,490) nm; $\lambda_{min}^{95\% EtOH}$ 248 (ε 1,290) nm; NMR ($CDCl_3$): δ 1.58 (singlet, 11b-methyl), 3.68 (singlet, 11-methyl), 4.47 (multiplet, C-5 proton) ppm.

Analysis: $C_{16}H_{18}N_2O$: Calculated: C, 75.56; H, 7.13; N, 11.02. Found: C, 75.51; H, 7.17; N, 11.16.

EXAMPLE IX 2,3,5,6,11,11b-hexahydro-11,11b-dimethyl-1H-indolizion-[8,7-b]indole, hydrochloride a. To a suspension of 3.00 g. lithium aluminum hydride in 100 ml. dry tetrahydrofuran (THF), under nitrogen, is added a solution of 9.15 g. 1,2,5,6,11,11b-hexahydro-11,11b-dimethyl-3H-indolizino[8,7-b]indol-3-one in 100 ml. dry tetrahydrofuran such that gentle reflux is maintained. Refluxing is continued for two hours after combining the reactants. The reaction mixture is cooled in an ice-water bath, treated dropwise with 16 ml. 3.0% w/v aqueous sodium hydroxide, stirred 0.25 hour, filtered and the solids are thoroughly washed with boiling tetrahydrofuran. Removal of solvent from the filtrate and washings yields a residue which is dissolved in 100 ml. 2N HCl and is washed with ether. The acidic solution is basified with 20 ml. concentrated ammonium hydroxide and the white precipitate is extracted into ether. After washing with water and with brine, the ethereal solution is dried (sodium sulfate) and freed of solvent. The crude base is chromatographically purified on a 400 g. column of neutral, activity III alumina to provide, from the 1:1 benzene-hexane eluates, 6.40 g. of 2,3,5,6,11,11b-hexahydro-11,11b-dimethyl-1H-indolizino[8,7-b]indole, m.p. 65°–68°C. Treatment of the base, in anhydrous ether, with excess isopropanolic hydrogen chloride affords a salt which is twice recrystallized from acetone, thus yielding the title compound, decomposition 226°–8°C., $\lambda_{max}^{KBr}$ 3.90, 4.12, 13.46 μ; $\lambda_{max}^{95\% EtOH}$ 224 (ε 35,100), 274 sh (ε 6,780), 281 (ε 7,030), 291 sh (ε 5.650 ) nm; $\lambda_{min}^{95\% EtOH}$ 245 (ε 2,040) nm. NMR ($CDCl_3$): δ 2.13 (singlet, 11b-methyl), 3.81 (singlet, 11-methyl) ppm.

Analysis: $C_{16}H_{20}N_2 \cdot HCl$: Calculated: C, 69.42; H, 7.65; Cl, 12.81; N, 10.12. Found: C, 69.43; H, 7.69; Cl, 13.04; N, 10.04.

b. Dry dimethylformamide (30 ml.), 1.81 g. 2,3,5,6,11,11b-hexahydro-11b-methyl-1H-indolizino[8,7-b]indole [S. Wawzonek and J. D. Nordstrom, *J. Med. Chem.*, 8, 265 (1965)] and 0.42 g. of about a 50% sodium hydride-mineral oil dispersion are stirred for ½ hour. The reaction mixture is cooled in an ice-water bath as 1.25 g. methyl iodide (0.55 ml.) in 3 ml. dry dimethylformamide are added dropwise. After stirring for 0.25 hour at 0°C., the mixture is kept at 25°C. for 7 hours. Solvent is removed in vacuo and the residue, dissolved in ether, is washed with water, brine and dried (sodium sulfate). Distillation of the solvent and purification of the residue on 60 g. neutral, activity III alumina provide, from the 1:1 benzenehexane eluates, a white solid. This amine is dissolved in 2N HCl, washed with ether and the acidic solution is basified with concentrated ammonium hydroxide. The precipitated base is extracted into ether, washed with water, brine and dried (sodium sulfate). Removal of solvent yields 1.07 g. 2,3,5,6,11,11b-hexahydro-11,11b-dimethyl-1H-indolizino[8,7-b]indole, m.p. 66.0°–68.5°C.; which, by infrared, ultraviolet and nuclear magnetic resonance spectral comparisons, is identical with the base prepared by the procedure of part (a) above.

EXAMPLE X 1,2,3,4,5,6,7,8-Octahydro-3,7,8-trimethylazonino-[5,4-b]indole, maleate (mono)

2,3,5,6,11,11b-Hexahydro-11,11b-dimethyl-1H-indolizino-[8,7-b]indole (3.56 g.), 50 ml. benzene and 21 g. methyl iodide are stirred two hours at about 25°C. Following removal of solvent, the residue is recrystallized (twice) from ethanol to afford 3.89 g. of 2,3,5,6-hexahydro-4,11,11b-trimethyl-1H-indolizino[8,7-b]indolium iodide, decomposition 196°–199°C.

Using the procedure of Example I-(a) and chromatographic purification of the crude product on neutral, activity III alumina, 8.40 g. 2,3,5,6,11,11b-hexahydro-4,11,11b-trimethyl-1H-indolizino[8,7-b]indolium iodide, 367 mg. lithium, 2 liters liquid ammonia and 2.38 g. 1-methoxy-2-propanol are converted to 4.67 g. of base, NMR (CDCl₃): δ 1.35 (doublet, J 7 cps., 7-methyl), 2.37 (singlet, 3-methyl), 3.67 (singlet, 8-methyl) ppm. Adding the base (in ether) to ethereal maleic acid (2.06 g.) and crystallization (twice) of the salt from isopropanol afford 5.45 g. of the title compound, decomposition 202°–204°C. (effervescence).

EXAMPLE XI 1,2,5,6,11,11b-Hexahydro-8-methoxy-11,11b-dimethyl-3H-indolizino[8,7-b]indol-3-one Sodium hydride (1.06 g. of about a 50% dispersion in mineral oil) is stirred under nitrogen with 5.41 g. 1,2,5,6,11,11b-hexahydro-8-methoxy-11b-methyl-3H-indolizino[8,7-b]indol-3-one [S. Wawzonek and J. D. Nordstrom, *J. Med. Chem.*, 8, 265 (1965)] in 100 ml. dry dimethylformamide for one-half hour. The brown solution is cooled in an ice-water bath as 3.41 g. methyl iodide (1.50 ml.) is added. After one-half hour of cooling, the reaction mass is allowed to stand at about 25°C. for sixteen hours. The dimethylformamide is removed in vacuo and the residue is twice triturated with 50 ml. hexane, dissolved in chloroform and washed with water. After drying (sodium sulfate), the solvent is removed and the solid is twice recrystallized from ethyl acetate, thus affording 4.30 g. of the title compound, m.p. 164°–7°C.; $\lambda_{max}^{CHCl_3}$ 6.02, 6.19 μ; NMR (CDCl₃); δ 1.60 (singlet, 11b-methyl), 3.68 (singlet, 11-methyl), 3.83 (singlet, methoxyl) ppm.

EXAMPLE XII 2,3,5,6,11,11b-Hexahydro-8-methoxy-11,11b-dimethyl-1H-indolizino[8,7-b]indole, hydrochloride 1,2,5,6,11,11b-hexahydro-8-methoxy-11,11b-dimethyl-3H-indolizino[8,7-b]indole-3-one (9.12 g.), 4.86 g. lithium aluminum hydride and 350 ml. dry tetrahydrofuran are reacted as in Example IX-(a). The residue isolated from the tetrahydrofuran fractions is dissolved in ether, washed with water and dried. Evaporation of the solvent gives a cream-colored solid which is twice crystallized from diisopropyl ether to yield 5.62 g. crystalline base, m.p. 113°–118°C. Treatment of 3.50 g. of the base in 150 ml. anhydrous ether with excess isopropanolic hydrogen chloride produces a salt that is twice recrystallized from absolute ethanol, thus yielding 3.25 g. of the title compound, decomposition 262°–264°C. (with effervescence), $\lambda_{max}^{KBr}$ 4.23, 6.20 μ.

EXAMPLE XIII 1,2,3,4,5,6,7,8-Octahydro-11-methoxy-3,7,8-trimethylazonino-[5,4-b]indole, maleate (mono)

2,3,5,6,11,11b-hexahydro-8-methoxy-11,11b-dimethyl-1 H-indolizino[8,7-b]indole (2.94 g.) and 50 ml. benzene and 7.81 g. methyl iodide are combined at about 25°C. After 1 hour, the solvent is removed and the residue is recrystallized (twice) from methanol to give 2.29 g. of 2,3,5,6,11,11b-hexahydro-8-methoxy-4,11,11b-trimethyl-1H-indolizino[8,7-b]indolium iodide, decomposition 242°–250°C.

Employing the method of Example I-(a), 6.28 g. 2,3,5,6,11,11b-hexahydro-8-methoxy-4,11,11b-trimethyl-1H-indolizino[8,7-b]indolium iodide, 1.5 l. liquid ammonia, 278 mg. lithium and 1.64 g. 1-methoxy-2-propanol are reacted to provide 3.30 g. of base as a yellow gum, NMR (CDCl₃): δ 1.35 (doublet, J 7 cps., 7-methyl), 2.37 (singlet, 3-methyl), 3.67 (singlet, 8-methyl), 3.81 (singlet, 11-methoxyl) ppm. The amine, in ether, is added to an ethereal solution of 1.30 g. maleic acid. Crystallization (twice) of the salt from ethanol yields 2.55 g. of the title compound, decomposition 198°–201°C. (effervescence).

What is claimed is:
1. 1,2,4,5,6,7,8,9-octahydro-3,9-dimethyl-3H-azecino[5,4-b]indole.
2. 1,2,3,4,5,6,7,8,-octahydro-3,8,-dimethylazonino[5,4-b]indole.
3. 1,2,3,4,5,6,7,8-octahydro-3,7,8-trimethylazonino[5,4-b]indole.
4. 1,2,3,4,5,6,7,8-octahydro-11-methoxy-3,7,8-trimethylazonino[5,4-b]indole.
5. 1,2,4,5,6,7,8,9-octahydro-3-methyl-3H-azecino[5,4-b]indole.
6. 1,2,3,4,5,6,7,8-octahydro-3-methylazonino]5,4-b]indole.

* * * * *